United States Patent
Cowley et al.

(10) Patent No.: US 9,795,657 B2
(45) Date of Patent: Oct. 24, 2017

(54) METHODS AND COMPOSITIONS FOR TREATING OXALATE-RELATED CONDITIONS

(75) Inventors: Aaron Cowley, Gainesville, FL (US); Qing-Shan Li, Gainesville, FL (US)

(73) Assignee: CAPTOZYME, LLC, Gainesville, FL (US)

(*) Notice: Subject to any disclaimer, the term of this patent is extended or adjusted under 35 U.S.C. 154(b) by 0 days.

(21) Appl. No.: 13/511,834

(22) PCT Filed: Nov. 23, 2010

(86) PCT No.: PCT/US2010/057805
§ 371 (c)(1),
(2), (4) Date: Dec. 26, 2012

(87) PCT Pub. No.: WO2011/066282
PCT Pub. Date: Jun. 3, 2011

(65) Prior Publication Data
US 2013/0108607 A1    May 2, 2013

Related U.S. Application Data

(60) Provisional application No. 61/281,907, filed on Nov. 25, 2009, provisional application No. 61/395,929, filed on May 20, 2010.

(51) Int. Cl.
| | |
|---|---|
| *A61K 38/44* | (2006.01) |
| *A61K 38/51* | (2006.01) |
| *A61K 9/00* | (2006.01) |
| *C12N 9/02* | (2006.01) |
| *A61K 38/00* | (2006.01) |

(52) U.S. Cl.
CPC ............ *A61K 38/51* (2013.01); *A61K 9/0053* (2013.01); *A61K 38/44* (2013.01); *C12N 9/0008* (2013.01); *C12Y 102/03004* (2013.01); *C12Y 401/01002* (2013.01); *A61K 38/00* (2013.01)

(58) Field of Classification Search
CPC .......... A61K 9/53; A61K 38/44; A61K 38/45; A61K 38/00; A61K 35/74; A61K 33/14; C12N 9/08; C12N 9/88; C12N 15/8282; C12N 9/06; C12N 15/8279; C12N 15/8257; C12Q 1/6895; C12Y 102/03004
See application file for complete search history.

(56) References Cited

U.S. PATENT DOCUMENTS

| | | | |
|---|---|---|---|
| 4,455,371 A | 6/1984 | Richardson et al. | |
| 6,200,562 B1 | 3/2001 | Allison et al. | |
| 6,242,230 B1 | 6/2001 | Batich et al. | |
| 6,699,469 B2 | 3/2004 | Allison et al. | |
| 7,807,623 B2 | 10/2010 | Pisegna et al. | |
| 2004/0234514 A1 | 11/2004 | Sidhu et al. | |
| 2005/0232901 A1 | 10/2005 | Zaghmout | |
| 2007/0178070 A1 | 8/2007 | Kaul et al. | |
| 2007/0184118 A1 | 8/2007 | Li et al. | |
| 2008/0038246 A1 | 2/2008 | Shenoy et al. | |
| 2008/0159988 A1 | 7/2008 | Zaghmout | |
| 2010/0028422 A1 | 2/2010 | Kaul et al. | |

FOREIGN PATENT DOCUMENTS

| | | |
|---|---|---|
| CN | 101554237 A | 10/2009 |
| EP | 2033651 A1 | 3/2009 |
| WO | WO 2010105491 A1 | 9/2010 |

OTHER PUBLICATIONS

Aguilar C. et al., Oxalate Oxidase from Ceriporiopsis subvermispora: Biochemical and Cytochemical Studies, Archives of Biochemistry and Biophysics, Jun. 15, 1999, vol. 366, No. 2, pp. 275-282.*

Micales J. A., Oxalate decarboxylase in the brown-rot wood decay fungus Postia placenta, Mat. Org., 1995, vol. 29, pp. 177-186.*

Svedruzic D. et al., The enzymes of oxalate metabolism: unexpected structures and mechanisms, Archives of Biochemistry and Biophysics, 2005, vol. 433, pp. 176-192.*

Berch S.M. et al., Development and potential of the cultivated and wild-harvested mushroom industries in the Republic of Korea and British Columbia, BC Journal of Ecosystem and Management, 2007, vol. 8, No. 3, pp. 53-75.*

Grujic, Danica et al., "Hyperoxaluria is reduced and nephrocalcinosis prevented with an oxalate-degrading enzyme in mice with hyperoxaluria", American Journal of Nephrology, Jan. 2009, vol. 29, No. 2, pp. 86-93.

Srivastava, S.K. et al., "An oxalic acid oxidase in the leaves of *Bougainvillea spectabilis*", The Biochemical Journal, Oct. 1962, vol. 85, pp. 33-38.

* cited by examiner

*Primary Examiner* — Satyendra K Singh (74) *Attorney, Agent, or Firm* — Timothy H. Van Dyke; Beusse, Wolter, Sanks & Maire PLLC (57) ABSTRACT

The subject invention relates in one aspect to an oxalate degrading composition, which includes at least one oxalate degrading enzyme. The composition includes an enriched insoluble component of fungal bio sample, and the composition is effective to degrade oxalate at a pH of 1.9 or higher. The composition is protected from protease degradation such as pepsin, trypsin and chymotrypsin. The composition is capable of withstanding the conditions of the stomach, small intestines, and/or large intestines of a subject.

8 Claims, 3 Drawing Sheets

Figure 1. The specific activity of OxDC from three fungi species at pH 2.0-6.0.

Figure 2. Thermal stability of OxDC from three fungi species.

Figure 3. The relative activity of OxOx from Bougainvillea buganvilla as a function of pH.

Figure 4. pH activity profile for OxDC from *Boletus flaviporus*, *Coprinus cometus*, and formulated OxDC from *Coprinus cometus*.

Figure 5. Soluble oxalate degradation by OxDC from *Agrocybe aegerita* in 3 food mixture samples with pH values of 2.3, 3.4 and 5.2.

METHODS AND COMPOSITIONS FOR TREATING OXALATE-RELATED CONDITIONS

CROSS-REFERENCE TO RELATED APPLICATIONS

This application is related to U.S. Provisional Application 61/281,907 filed Nov. 25, 2009 and U.S. Provisional Application 61/395,929 filed May 20, 2010 to which priority is claimed under 35 USC 119.

STATEMENT REGARDING FEDERALLY SPONSORED DEVELOPMENT

This invention was made with government support under Grant Number 1R43AT006065-01 awarded by the National Center for Complementary and Alternative Medicine (NC-CAM), National Institute of Health (NIH). The Government has certain rights in the invention.

BACKGROUND

Approximately 3 million people visit health care providers each year for kidney stones. Of those 3 million patients, in the United States more than one half million suffer from kidney stone-related conditions. Kidney stones are a very common and painful urinary tract disorder. The most common type of stone contains calcium in combination with either oxalate or phosphate, in which approximately 70% is calcium oxalate. (Tsujihata, M. (2008) Mechanism of calcium oxalate renal stone formation and renal tubular cell injury, *Int J Urol* 15, 115-120; Daudon, M., Dore, J. C., Jungers, P., and Lacour, B. (2004) Changes in stone composition according to age and gender of patients: a multivariate epidemiological approach, *Urol Res* 32, 241-247.) Many disease states are associated with an excess quantity of oxalate in the body including: primary hyperoxaluria, secondary hyperoxaluria, autism, vulvodynia, oxalosis associated with end-stage renal disease, cardiac conductance disorders, Crohn's disease, inflammatory bowel disease, colitis, urolithiasis, oxalosis associated with end-stage renal disease, sarcoidosis, asthma, COPD, fibromyalgia, Zellweger syndrome, bariatric surgery and other enteric disease states.

Oxalate is normally produced in plants, and is primarily found in leaves, nuts, fruits and barks. In food products, oxalate is found in high levels particularly in plant foods including: vegetables, cereal grains, nuts, beans and beverages. A typical daily intake of oxalate is between 80-120 mg/day, but can range from 44-350 mg/day. Dietary oxalate may form sodium, potassium or calcium salts in food.

Oxalate may be absorbed throughout the entire gastrointestinal tract (GI tract) including the stomach, and the small and large intestines. Therefore, removal of dietary oxalate in these organs is effective in preventing oxalate absorption. Absorption of dietary oxalate contributes to 10-70% of urinary oxalate secretion, likely a crucial contribution to urinary calcium oxalate supersaturation. (Holmes, R. P., Goodman, H. O., and Assimos, D. G. (2001) Contribution of dietary oxalate to urinary oxalate excretion, *Kidney Int* 59, 270-276.) It is believed that calcium oxalate supersaturation is the determining driving force of calcium oxalate stone formation. Therefore, by reducing calcium oxalate supersaturation, the risk of stone formation will likely be significantly decreased.

There are very few, if any, treatment strategies known to significantly decrease the risk of stone formation by reducing or eliminating the absorption of dietary oxalate in the system. One way to limit dietary oxalate absorption would be to orally administer oxalate degrading enzymes which come into contact with the stomach and the small and large intestines. The challenge in providing such treatment is the harsh acidic stomach environment, making it difficult for an enzyme to survive and function at a low pH and in a high pepsin activity environment. The small and large intestines also provide a challenging environment for the survival of an enzyme due to the high levels of trypsin and chymotrypsin activity. The pH in the stomach is affected by several factors including individual stomach health-related conditions, and quantity and substance of meals. These factors may result in a broad stomach pH range between 1.9-5.5. The pH in the human stomach is non-homogenous due to the presence of acid pockets. Hence, it is critical to find an oxalate-degrading enzyme that is stable and potent within this acidic pH range to be an effective treatment for humans. Additionally, the oxalate degrading enzyme must be stable within a pH range of 5.5-8.0 that can withstand the conditions of the intestinal tract. The oxalate degrading enzyme must be protected from pepsin digestion in the stomach as well as from trypsin and chymotrypsin in the small and large intestines.

SUMMARY

The subject invention provides in one embodiment, an oxalate degrading composition including at least one oxalate degrading enzyme. The composition includes an enriched insoluble component of fungal biosample, and is effective to degrade oxalate at a pH of 1.9 or higher. The term "biosample" as used herein refers to a plurality of cells or cell-containing tissue(s) from a species of interest. In a typical embodiment, a biosample is homogenized or otherwise disrupted so as to break apart or lyse cells in the biosample. OxDC and OxOx are generally found in the insoluble component of cells, i.e. the proteins and other structures (cell wall/membranes) in cells that are not water-soluble. The insoluble component of a biosample can be enriched by removing at least a portion of the water and water-soluble cellular components from the water-insoluble components. Enrichment of the insoluble component can occur by means conventional in the art such as filtration, centrifugation, lyophilization and/or simple drying. In another embodiment, there is provided a method for reducing the amount of oxalate in a subject. The method includes administering a therapeutically effective amount of a composition including at least one oxalate degrading enzyme to the subject. The at least one oxalate degrading enzyme includes an enzyme that is active at a pH level of 1.9-6.3, such that the enzyme degrades soluble oxalate in the digestive tract of the subject.

In another embodiment, there is provided a method for preventing/treating an oxalate-related medical condition in a subject. The method includes administering a therapeutically effective amount of at least one oxalate degrading enzyme containing composition to a subject in need. The oxalate-related medical condition includes one of: primary hyperoxaluria, autism, secondary hyperoxaluria, Crohn's Disease, inflammatory bowel disease, colitis, cardiac conductance disorder, urolithiasis, vulvodynia, bariatric surgery, sarcoidosis, asthma, COPD, fibromyalgia, Zellweger syndrome, oxalosis associated with end-stage renal disease, and other enteric disease states.

In a further embodiment, an article of manufacture including packaging material and an effective amount of oxalate degrading enzyme is provided. The packaging material includes at least one of: pills, candy, sachet, tablet, in bulk, bar, and/or a food additive.

In yet a further embodiment, a method for treating an oxalate-related medical condition is provided. The method includes coadministering to a subject in need of such treatment a therapeutically effective amount of a first composition, wherein the first composition releases enzymes in the stomach of the subject and a second composition, wherein the second composition releases enzymes in the intestinal tract of the subject. The method provides that when the enzymes are released, the first composition degrades oxalate in the stomach, and second composition degrades oxalate in the intestinal tract.

In still a further embodiment, an oxalate degrading composition derived from a fungal source is provided. The composition includes at least a first composition and a second composition. The first composition includes at least one oxalate degrading enzyme, wherein the first composition releases the at least one oxalate degrading enzyme at a pH within a pH range of 1.9-6.3. The second composition includes at least one oxalate degrading enzyme, wherein said second composition releases the at least one oxalate degrading enzyme at a pH within a pH range of 5.5-8.0.

In another embodiment, an article of manufacture comprising packaging material and an effective amount of oxalate degrading enzyme is provided. The article of manufacture includes a first composition, wherein the first composition is operable at a pH within a first pH range. The article of manufacture also includes a second composition, wherein the second composition is operable at a pH within a second pH range. The article of manufacture includes at least a first oxalate degrading enzyme and a second oxalate degrading enzyme.

DETAILED DESCRIPTION

The invention is based on the inventors' pursuit of developing new compositions for degrading oxalate in a subject. OxDC activity has been evaluated in over one-hundred twenty different mushroom species entailed by this invention as provided in Example 2. Many of them are edible or medicinally used mushrooms. OxDC activity from many of these mushroom fungi are stable and active from pH 1.9-2.5, 2.5-3.0, 3.0-3.5, 3.5-4.0, 4.0-4.5, 4.5-5.0, 5.0-5.5, 5.5-6.0 and 6.0-6.3, and protected from pepsin digestion. Furthermore, some strains of fungi are stable and show OxDC activity at temperatures exceeding 70° C. This property is very helpful at predicting stability. Therefore, this present invention comprises these pH and thermally stable oxalate degrading enzymes.

Accordingly, in one embodiment of the subject invention, there is provided an oxalate degrading composition including at least one oxalate degrading enzyme. The composition includes an enriched insoluble component of fungal biosample, and is effective to degrade oxalate at a pH of 1.9 or higher. Another aspect of the subject invention provides a composition in which at least one oxalate degrading enzyme includes an enzyme that is formulated and active at a pH within a pH range of 1.9-5.5, and/or a second enzyme that is active at a pH within a pH range of 5.0-8.0 or a combination of the first and second enzymes. In a more specific embodiment of the subject invention, a composition is included in which the enzyme comprises at least one of: oxalate-oxidase (OxOx), and/or oxalate decarboxylase (OxDC).

Oxalate decarboxylase (OxDC) is an enzyme that degrades oxalate. OxDC compositions disclosed herein typically come from edible or non-poisonous fungi has ideal properties to be a potential therapeutic or medical food or dietary supplement or other treatment strategy as they are stable and active at exemplary pH levels of 1.9-2.5, 2.5-3.0, 3.0-3.5, 3.5-4.0, 4.0-4.5, 4.5-5.0, 5.0-5.5, 5.5-6.0. OxDC compositions of the invention can be intracellular or it may be membrane-bound or otherwise associated with the cell wall. The state of OxDC compositions from pepsin digestion, and is capable of degrading the majority of ingested oxalate in the stomach, the small intestines and the large intestines. OxDC can be prepared from mycelia of fungi grown by fermentation, or from fruit bodies or mushrooms formed by these fungi. These fungal mycelia or cleaned mushrooms or fruit bodies containing OxDC can be made into a solution, powder, or other formulation by means of grinding, mashing, suspending, mixing or other appropriate treatment as known by those skilled in the art. The mycelia, mushroom, or fruit body preparation can then be dried and formulated into tablets or capsules or packaged into sachets or made into bars or made into candy or incorporated into food compositions or other means of appropriate distribution as known by those skilled in the art. In one aspect, the oxalate degrading composition of the subject invention can be taken with meals and oxalate containing snacks. Such a product has a wide application within the calcium oxalate stone-forming population or other conditions related to oxalate in humans and non-humans. Such composition is in one particular aspect designed to degrade non-systemic oxalate, oxalate in the GI tract, notably in the stomach, and prevent exogenous oxalate (e.g. from food) from entering the systemic circulation. In a more specific embodiment, the enzyme is active and stable from pH 1.9-6

According to an alternative embodiment, an oxalate degrading enzyme is active at pH of 3.0-6.5 when found associated to the cell wall but that is active from ph 3.0-7.0 when purified and formulated into particles. According to another alternative embodiment, oxalate degrading enzyme containing composition includes a first enzyme stable and active in the stomach and a second enzyme stable in the stomach but only active in the intestinal tract.

Another class of oxalate degrading enzymes, oxalate-oxidase (OxOx), is expressed in higher plants and fungi and catalyzes the oxygen dependent oxidation of oxalate to $CO_2$ with concomitant formation of $H_2O_2$. An aspect of the present invention relates to the many oxalate oxidase (OxOx) enzymes found in plants and fungi that are stable and as described above active at exemplary pH levels of 1.9-2.5, 2.5-3.0, 3.0-3.5, 3.5-4.0, 4.0-4.5, 4.5-5.0 and 5.0-5.5. A particular OxOx enzyme from *Bouganvillea buganvillea* has been shown to be active from pH 5.5-8.0.

These OxOx and OxDC enzymes can be prepared directly from these plants or fungi or from the genes encoding OxOx and OxDC, respectively, by cloning of these genes, subcloning into a recombinant expression system including, but not limited to, *E. coli*, bacteria, yeast, fungi and mammalian cells by using appropriate procedures commonly accepted.

After purified, the expressed OxOx enzyme can be formulated to resist pepsin digestion in the stomach and trypsin and chymotrypsin in the small and large intestines by various methods including, but not limited to, microencapsulation, attaching to large molecules such as PEG, or by modifying the molecular surface of the OxOx enzyme. The formulated enzyme can be made into, but are not limited to, a tablet, capsule, sachets, candy, bar, or incorporated into other food compositions or other formulations for various modes of distribution. Thus, the present invention relates to a composition, wherein these oxalate-degrading enzymes are embedded in a polymeric material, which protects the enzymes from degradation under gastric conditions. The fungal mycelia or cleaned mushrooms or fruit bodies or plant materials containing OxOx are made into a solution, powder, or other physical appearance by means of grinding, mashing, suspending, mixing or other appropriate treatment as known by those skilled in the art. The mycelia, mushroom, or fruit body preparation, or plant material is then dried and formulated into tablets or capsules or packaged into sachets or or made into bars or made into candy or incorporated into other food compositions or other means of appropriate distribution as known by those skilled in the art.

In another embodiment, an article of manufacture is provided, which includes packaging material and an effective amount of oxalate degrading enzyme. The packaging material comprises at least one of: pills, candy, sachet, tablet, in bulk, bars, and/or a food additive.

In yet a further embodiment, an article of manufacture comprising packaging material and an effective amount of oxalate degrading enzyme is provided. The article of manufacture includes a first composition, wherein the first composition is operable at a pH within a first pH range, and a second composition, wherein the second composition is operable at a pH within a second pH range. The article of manufacture includes at least a first oxalate degrading enzyme and a second oxalate degrading enzyme. The first oxalate degrading enzyme may include a first component of an oral unit, and the second oxalate degrading enzyme may include a second component of an oral unit. The first component of the oral unit may surround the second component of the oral unit, or vice versa. The first pH range includes a pH of 1.9-5.5 and the second pH range includes a pH of 5.5-8.0. In a specific embodiment, the article of manufacture relates to a two-component pill or tablet, wherein a first component is contained within a second component. The term "oral unit" as used herein refers to an individual, predetermined dosage amount in a solid, semi-solid, and/or liquid form of a size and shape suitable for oral administration. Examples of oral units include, but are not limited to, capsules, tablets, pills, liquid suspensions, powders, lozenge, etc. Also, an oral unit can refer to a predetermined amount of a composition provided in an ampoule or packet, or other container that is opened to release its contents for oral administration.

As used herein, the terms "subject" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human.

In alternative embodiments, the present invention relates to OxDC that can be produced by recombinant expression. An aspect of the present invention relates to the many oxalate decarboxylase (OxDC) enzymes found in plants and fungi that are active at exemplary pH levels of 5.0-5.5, 5.5-6.0, and 6.0-6.5. Genes encoding OxDC from these fungi can be cloned and heterogeneously expressed in, but not limited to, *E. coli*, bacteria, yeast, fungi, or mammalian cells using appropriate procedures commonly accepted by people skilled in the art. Recombinant OxDC that is cloned, subcloned, and expressed by, but not limited to, *E. coli*, bacteria, yeast, fungi, or mammalian cells can be purified by chromatography methods and many other available methods that are well known by people in the field. The purified OxDC can be further formulated into a product to be protected from pepsin, trypsin and chymotrypsin digestion and achieve other beneficial properties including long shelf lifetime and a broader pH activity profile. Formulation can result in the OxDC enzyme being active from pH levels of 5.0-5.5, 5.5-6.0, 6.0-6.5, and 6.5-7.0.

In another embodiment, the present invention relates to the second class of oxalate degrading enzymes, oxalate oxidase (E.C.1.2.3.4, OxOx), which is expressed in higher order plants. This enzyme catalyzes the oxygen dependent oxidation of oxalate to CO2 and produces $H_2O_2$ during seed germination or during defense from parasite invasions. Some fungi have been reported to produce this enzyme as well. Indeed, several fungi tested under this invention show OxOx activity. OxOx from several plants and fungi tested under this invention, are stable and active at pH 1.9-5.5, and suitable to degrade dietary oxalate in the human stomach. Other OxOx enzymes from several plants and fungi tested under this invention, are active from pH 5.0-8.5, and suitable to degrade dietary oxalate in the non-human stomach, and small and large intestines.

The present invention relates to the OxOx enzyme from plants and fungi that can be directly prepared from these organisms. Plants or fungi can be grown under conditions to achieve high OxOx content. The manufacturing process can be similar to other food production processes including, but not limited to, cleaning, sanitation, milling, drying and packaging.

In an alternative embodiment, the present invention relates to the OxOx enzyme that can be produced through recombinant expression. Genes encoding OxOx from these plants or fungi can be cloned and heterogeneously expressed in, but not limited to, *E. coli*, bacteria, fungi or yeast and other kinds of plants. Plants equipped with recombinant OxOx can be used as raw materials in the similar manner as using plants, which express OxOx naturally. Recombinant OxOx expressed by, but not limited to, *E. coli*, bacteria, fungi or yeast or other appropriate system of expression can be purified with commonly accepted procedures and further formulated into a final product.

In yet another embodiment, the present invention relates to the OxOx or OxDC enzyme dry powder or solution or other physical appearance that can be manufactured into various means of distribution including, but not limited to, tablets, capsules, various kinds of candy or bars, sachets, or directly as a powder.

In another embodiment, a composition is provided in which the at least one oxalate degrading enzyme are derived from cell samples of the following: *Dentinum reparandum, Russula virescens, Armillaria tabescens, Cantharellur cinnabarinur, Boletur rubellus* var *fraternus, Collybia acer-* vata, *Crepidotus mollis, Boletur subglabnpes, Boletus ornatipes, Polyporus elegans, Pluteus cervinus, Sderoderma citrinum, Pleurotus ostreatus, Xerula radicata, Telephoro vlalis, Clitocybe, Cortinarius cedretorun, Lactarius indigo, Russula densifolia, Amanita rhopalopus, Clitocybe hydrograma, Amanita gemmata, Cortinarius lewisii, Pleurotus eryngii, Inocybe rimosa, Lactarius atrorividus, Russula cyanoxhanth, Sderoderma polyrhizum, Lentinula edodes, Hypsizygus tessellates, Flammulina velutipes, Leucangia carthusiana, Tuber oregonese, Grifola frondosa, Boletus rubricitrinus, Boletus fraternus, Gyroporus subalbellus, Leucoagaricus americanus, Omphalotus olearius, Coprinus disseminates, Amanita brunnescens, Russula* helerophylla, Mycorrhaphium adustum, Armillaria tabescense, Boletus flawporus, Russula pectintoides, Lentinula boryana, Amanita mutabilis, Gyroporus subalbellus 2nd, *Collybia peronata, Lactarius corrugis, Rhodocybe, Macrocybe titaus, Collybia, Pluteus, Lactarius yazooensis, Leccinum insigne, Coprinus comatus, Polyporus tuberaster, Agrocybe aegerita, Trametes versicolor, Ganoderma lucidum, Hypsizygus ulmarius, Lentinula edodes* (warm), *Lentinula edodes* (cold), *Lentinula edodes* (wide range), *Russula amoenolens, Lactarius tomentosu*, and/or *Agaricus blazei*. Optimum pH ranges of OxDC and/or OxOx from these select fungi were found between 1.9-6.3. Active pH ranges of OxDC and/or OxOx from these select fungi were found between 1.9-6.3, as noted in Table 1.

TABLE 1

Optimum and Active pH Ranges of OxDC or OxOx from Select Fungi

| Names | Optimum pH range | Active pH range |
| --- | --- | --- |
| *Dentinum repandum* | 1.9-3.2 | 1.9-4.3 |
| *Russula virescens* | 1.9-2.7 | 1.9-4.3 |
| *Boletur rubellus* var *fraternus* | 1.9-3.2 | 1.9-4.3 |
| *Crepidotus mollis* | 3.2-4.3 | 1.9-5.3 |
| *Polyporus elegans* | 1.9-2.7 | 1.9-3.2 |
| *Scleroderma citrinum* | 1.9-3.2 | 1.9-5.3 |
| *Xerula radicata* | 2.7-3.2 | 1.9-5.3 |
| *Thelephora vlalis* | 1.9-2.7 | 1.9-4.8 |
| *Lactarius indigo* | 1.9-3.2 | 1.9-4.3 |
| *Russula densifolia* | 1.9-3.2 | 1.9-4.3 |
| *Pleurotus eryngii* | 3.5-4.5 | 3.2-5.3 |
| *Inocybe rimosa* | 2.7-3.2 | 1.9-4.8 |
| *Lactarius atrorividus* | 1.9-3.2 | 1.9-4.3 |
| *Scleroderma polyrhizum* | 1.9-3.2 | 1.9-4.3 |
| *Lentinula edodes* | 2.5-3.0 | 1.9-5.5 |
| *Hypsizygus tessellatus* | 3.5-4.0 | 2.5-5.5 |
| *Hypsizygus tessellatus* | 3.5-4.0 | 2.5-5.5 |
| *Flammulina velutipes* | 2.7-4.0 | 1.9-5.5 |
| *Leucangia carthusiana* | 2.7-4.0 | 1.9-5.5 |
| *Tuber oregonense* | 2.7-4.0 | 1.9-5.5 |
| *Grifola frondosa* | 2.7-3.2 | 1.9-3.2 |
| *Boletus rubricitrinus* | 1.9-2.7 | 1.9-3.2 |
| *Boletus fraternus* | 1.9-3.2 | 1.9-5.3 |
| *Gyroporus subalbellus* | 1.9-3.2 | 1.9-5.3 |
| *Leucoagaricus americanus* | 1.9-3.2 | 1.9-4.3 |
| *Omphalotus olearius* | 1.9-4.3 | 1.9-5.3 |
| *Coprinus disseminates* | 2.7-3.2 | 1.9-4.3 |
| *Amanita brunnescens* | 2.7-3.2 | 1.9-4.3 |
| *Mycorrhaphium adustum* | 1.9-2.7 | 1.9-4.3 |
| *Armillaria tabescense* | 2.7-3.2 | 1.9-4.3 |
| *Boletus flaviporus* | 2.7-5.3 | 1.9-6.3 |
| *Russula pectintoides* | 1.9-4.3 | 1.9-5.3 |
| *Amanita mutabilis* | 2.7-3.2 | 1.9-5.3 |
| *Gyroporus subalbellus* $2^{nd}$ | 1.9-3.2 | 1.9-5.3 |
| *Collybia peronata* | 1.9-3.2 | 1.9-4.3 |
| *Rhodocybe* | 1.9-3.2 | 1.9-4.3 |
| *Macrocybe titaus* | 2.7-3.2 | 1.9-4.3 |
| *Lactarius yazoensis* | 2.7-4.3 | 1.9-5.3 |
| *Leccinum insigne* | 2.7-3.2 | 1.9-4.8 |
| *Coprinus comatus* | 3.2-6.0 | 1.9-6.3 |
| *Polyporus tuberaster* | 1.9-3.2 | 1.9-4.8 |
| *Agrocybe aegerita* | 2.7-3.7 | 1.9-6.3 |
| *Trametes versicolor* | 1.9-2.3 | 1.9-4.3 |
| *Ganoderma lucidum* | 1.9-2.7 | 1.9-4.5 |
| *Hypsizygus ulmarius* | 3.0-4.0 | 1.9-6.3 |
| *Lentinula edodes* (warm) | 2.5-3.0 | 1.9-5.5 |
| *Lentinula edodes* (cold) | 2.5-3.0 | 1.9-5.5 |
| *Lentinula edodes* (wide range) | 2.5-3.0 | 1.9-5.5 |
| *Agaricus blazei* (OxOx) | 2.5-3.0 | 1.9-4.8 |
| *Lactarius tomentosu* (OxOx) | 2.5-3.0 | 1.9-4.3 |

In a more specific embodiment, the invention relates to OxDC and/or OxOx from these fungi that can be directly made from mycelia. Mycelia can be produced by fermentation technology. Fermentation processes for growing fungi is well developed and known by people skilled in the art. The fermentation process development includes medium optimization and fermentation process control parameters, optimization to achieve optimum fungal growth, and an induction method optimization to achieve maximum OxDC and/or OxOx production. The medium optimization, fermentation process optimization, and induction process optimization may vary with specific fungal species. It is well known by people in the field, that different fungi may require different medium compositions, temperature, and pH to grow, and require different induction conditions to produce OxDC and/or OxOx, such as pH range. OxDC and/or OxOx produced from these mycelia can be presented as, but not limited to, dry powder, solutions or other physical appearance by means of grinding, mashing, suspending, mixing or other appropriate treatment. After harvesting, these mycelia can be dried and milled into powder or other physical appearance.

In a more particular embodiment, a composition is provided where the at least one oxalate degrading enzyme is obtained from two or more of: *Flammulina velutipes, Agrocybe aegerita*, and *Coprinus comatus*, or any combination thereof, wherein the composition is active at a pH of 1.9-6.3.

In an alternative embodiment, a method for reducing the amount of oxalate in a subject is provided. The method includes administering a therapeutically effective amount of a composition including at least one oxalate degrading enzyme to the subject. The at least one oxalate degrading enzyme includes an composition that is active at a pH level of 1.9-6.3, wherein the enzyme degrades soluble oxalate in the digestive tract of the subject. In a more particular embodiment, the therapeutically effective amount of the composition is orally administered to the subject. In a further embodiment, the at least one oxalate degrading enzyme comprises at least one of: oxalate-oxidase (OxOx), and/or oxalate decarboxylase (OxDC).

According to other embodiments, the present invention comprises methods to administer compositions comprising oxalate degrading enzymes to the stomach and later the small and large intestines, and such compositions are useful for degrading dietary oxalate as well as systemic oxalate and aiding in preventing the uptake of oxalate from the stomach and intestinal tract, which provides methods for treatment and prevention of oxalate-related diseases and disorders, such as, e.g., hyperoxaluria, primary hyperoxaluria, idiopathic calcium oxalate kidney stone disease (urothiliasis), and absorptive and enteric hyperoxaluria. The compositions comprise polymeric or copolymeric materials so that the administered enzymes are protected from the protein degradation and/or pH or acidic dependent degradation occurring under gastric conditions of the stomach, i.e. low pH and the presence and activity of pepsin as well as trypsin and chymotrypsin within the small and large intestines.

In specific embodiments, the present invention comprises compositions, wherein the oxalate reducing enzymes are combined in a polymeric material, which protects the enzymes from degradation under gastric conditions and/or also under intestinal conditions. It can be envisaged that this composition may comprise any enzymes or cofactors, and the present invention contemplates compositions that comprise oxalate degrading enzymes, such as, oxalate decarboxylase, oxalate oxidase, or a combination of oxalyl-CoA decarboxylase and formyl CoA transferase, or a combination of any of these.

Since there is evidence indicating that absorption of dietary oxalate has a significant contribution to urinary calcium oxalate supersaturation, any treatment strategy that significantly reduces the absorption of dietary oxalate in stone formers is likely to decrease the risk of stone formation. Clinical trials with calcium supplemented diets, to bind oxalate and thus limit oxalate absorption, have showed a reduction in the absorption of dietary oxalate. However, this likely results in more calcium absorption from the diet and thus an increased risk of stone formation in certain individuals. The inventors have discovered that embodiments of the invention possess the ability to avoid modifying urinary chemistry parameters such as pH or calcium concentration; thereby, reducing risks of uric acid or phosphate stone formation.

*O. formigenes*, an anaerobic organism that colonizes the large intestine of animals and humans and uses oxalate as its sole energy source, has been evaluated as a therapeutic to treat primary hyperoxaluria. However, the mode of action of *O. formigenes* prevents it from acting as a dietary oxalate intercept. Therefore, OxDC from *Bacillus subtilis* was evaluated to reduce dietary oxalate. Reduction of dietary oxalate absorption by using this enzyme has been tested in mice, rats and healthy human volunteers. Urinary oxalate from both mice and rats was significantly lower (~50%) than controls, but there was no significant urinary oxalate reduction in a double-blind placebo-controlled healthy human volunteer dose escalation study. A likely explanation, is that the enzyme is inactivated in the human stomach due to the acidic environment of the stomach. This argument is supported by the fact that the fasted rat stomach is ~pH 4.0, while the fasted human stomach is ~pH 1.5.

After meal consumption, the human stomach pH increases to a broad pH range of 2.0-5.5, which varies with meal contents and amounts, individual stomach conditions, and the amounts of stomach juice in the stomach. Further, its widely regarded that the pH is non-homogenous due to acid pockets, meaning the pH in places close to acid pockets may be far lower than the average pH of the stomach. OxDC from *Bacillus subtilis* loses its activity in less than one minute when exposed to a pH 3.0 or lower.

Therefore, to be an effective treatment for humans or non-humans it is crucial for oxalate-degrading enzymes to be stable, pepsin resistant, trypsin resistant, and/or chymotrypsin resistant and active, degrade most available (5-10, 10-20, 20-30, 30-40, 40-50, 50-60, 60-70, 70-80, 80-90, or 90-100%) ingested oxalate in the stomach within the gastric emptying time, at this acidic pH range of 1.9-2.5, 2.5-3.0, 3.0-3.5, 3.5-4.0, 4.0-4.5, 4.5-5.0, 5.0-5.5, 5.5-6.0 and 6.0-6.3 to cover the majority of situations that are likely to occur in the human or non-human stomach and duodenum to be an effective treatment for humans and non-humans. Furthermore, at low pH, more oxalate is soluble and available for absorption. Thus, an enzyme, which is stable, protease (pepsin, trypsin, chymotrypsin etc) resistant, and active at low pH is crucial to be able to reduce soluble oxalate in the stomach and duodenum acidic environments of humans and non-humans and hence decrease oxalate absorption.

According to other embodiments, the present invention comprises compositions of the two classes of oxalate-degrading enzymes that may be stable and active from pH 2.0-5.5 and/or pH 5.0-8.5, oxalate decarboxylase and oxalate oxidase. Oxalate decarboxylase (EC 4.1.1.2), requires a catalytic amount of oxygen to convert oxalate to formate and carbon dioxide and is widely distributed in bacteria and fungi. OxDC from *B. subtilis* is the most studied bacterial OxDC. The enzyme is encoded by the YvrK gene in *B. subtilis*. The gene was cloned and expressed in *E. coli*, and was demonstrated to be potent at degrading oxalate. Recombinant OxDC has been well characterized by biophysical and biochemical analysis as well as x-ray crystallography. However, this specific OxDC is unstable at pH below 3.2, making it difficult to remain folded and capable to degrade dietary oxalate within the human stomach. Studies of bacterial oxalate decarboxylase at enzymology level are largely limited to the YvrK gene product, but a search of Pubmed with the term "oxalate decarboxylase" revealed 490 entities from bacteria and 172 entries from fungi as of Nov. 8, 2010, indicating an abundance of genes encoding OxDC or putative OxDC throughout bacteria. OxDC is widely distributed in the fungal kingdom as well. From the hundred and twenty or more fungal species tested in this invention, the majority were found to contain oxalate-degrading activity (specifically OxDC activity). Even for those, which did not show OxDC activity as evaluated under the tests outlined in this invention, they may contain oxalate-degrading activity as well, if considering that their oxalate-degrading activity might be lost during the material production or storage, or if the oxalate-degrading enzymes are only expressed under certain phases of its life cycle. This observation is further supported by literature that a search of Pubmed with the term "oxalate decarboxylase" revealed 172 entities from fungi as of Nov. 8, 2010, further indicating that OxDC is a common enzyme in the fungal kingdom. Some of the OxDC enzymes and the products of these genes may be stable and active in the pH range of 1.9-2.5, 2.5-3.0, 3.0-3.5, 3.5-4.0, 4.0-4.5, 4.5-5.0 and 5.0-5.5, or be stable and active in the pH range of 5.0-5.5, 5.5-6.0, 6.0-6.5, 6.5-7.0, 7.0-7.5, and 7.5-8.0. Therefore, this present invention comprises compositions containing such stable oxalate degrading enzymes.

Determination of a Therapeutically Effective Dose

An oxalate-degrading composition embodiment of the invention is administered in a desired amount, such as an amount that is sufficient to degrade substantially all oxalate normally present in a standard meal. Depending on the food choices, an average Western diet can contain 100 to 300 mg of oxalate/day.

A therapeutically effective amount may comprise an amount of activity units of oxalate-reducing enzyme activity that will reduce a portion of the oxalate present, or a level of activity units of oxalate-reducing enzyme activity that will initiate a reduction in the amount of oxalate or maintain a lowered amount of oxalate in the individual, compared to the amount of oxalate present before administration of the composition. The number of activity units of oxalate-reducing enzyme activity that can be used in a single dose composition can range from about 0.0001 units to about 10,000 units, from about 5 units to 100 units, from 0.05 to 50 units, to 0.5 to 500, from about 0.01 units to about 50 units, from about 0.01 units to about 5 units, from about 1 units to about 100 units, from about 25 units to about 50 units, from about 30 units to about 100 units, from about 40 units to about 120 units, from about 60 units to about 15, from about 50 units to about 100 units, from about 100 units to about 500 units, from about 100 units to about 300 units, from about 100 units to about 400 units, from about 100 units to about 10,000 units, from about 1,000 units to about 5,000 units, from about 2,500 units to about 10,000 units, from about 0.001 units to about 2,000 units and all ranges encompassed therein. A unit of the enzyme is the amount of enzyme that will degrade one micromole of oxalate per minute at 37° C. Also, the unit ranges above relate to the number of units per gram of composition.

Additionally, a composition according to the present invention may comprise enzymes that comprises modifications or mutations, including, but not limited to, chimeras formed using domains comprising the oxalate degrading active site of an oxalate reducing enzyme, or peptide fragments notably those comprising of the active sites; modifications or mutations, including but not limited to, deletions, insertions, replacements, reversions, mutations for increased activity, substitution of naturally occurring amino acids with non-natural amino acids, or other modifications known to those skilled in the art.

Compositions which exhibit large therapeutic indices are generally desired. The data obtained from cell culture assays and animal studies are used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosages used in method embodiments can be adjusted, in light of factors related to the subject that requires treatment, to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

In certain embodiments, normal dosage amounts can vary from 0.1 to 100,000 micrograms, up to a total dose of about 50 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Compositions and Administration

The invention provides compositions which can be administered to a patient to achieve a therapeutic effect. Compositions of the invention can comprise, for example, oxalate-oxidase (OxOx), and/or oxalate decarboxylase (OxDC). The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones. As noted above, composition embodiments may comprise polymeric or copolymeric materials so that the administered enzymes are further protected from the protein degradation and/or pH or acidic dependent degradation occurring under gastric conditions of the stomach, i.e. low pH and the presence and activity of pepsin.

In addition to the active ingredients, these pharmaceutical compositions can contain suitable pharmaceutically acceptable carriers comprising excipients and auxiliaries which facilitate processing of the active compounds into preparations which can be used pharmaceutically. Compositions of the invention are typically administered via oral administration, but it is conceived that other routes of administration might be developed as well, including, but not limited to, intravenous, intramuscular, intra-arterial, intramedullary, intrathecal, intraventricular, transdermal, subcutaneous, intraperitoneal, intranasal, parenteral, topical, sublingual, or rectal means. Compositions designed for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Compositions for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Preparations which can be used orally include push fit capsules made of gelatin, as well as soft, sealed capsules made of gelatin and a coating, such as glycerol or sorbitol. Push fit capsules can contain active ingredients mixed with a filler or binders, such as lactose or starches, lubricants, such as talc or magnesium stearate, and, optionally, stabilizers or maybe by themselves. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

Pharmaceutical preparations using oxalate degrading enzyme compositions contemplated herein can be manufactured in a manner that is known in the art, e.g., by means of conventional mixing, dissolving, granulating, dragee making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base font's. In other cases, the preferred preparation can be a lyophilized powder which can contain any or all of the following: 150 mM histidine, 0.1%2% sucrose, and 27% mannitol, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

In any of the embodiments described above, any of the compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

In a particular embodiment, the enzyme is oxalate-oxidase. In a further embodiment, the enzyme is isolated from a fungal source. In another embodiment, the enzyme is oxalate decarboxylase. In a further embodiment, the enzyme is isolated from a fungal or bacterial source. In a particular embodiment, the at least one oxalate degrading enzyme comprises an enzyme that is active at a pH of 1.9-6.3. In another embodiment, the at least one oxalate degrading enzyme comprises an enzyme that is active at a pH of 5.8-8. In a particular embodiment, the at least one oxalate degrading enzyme is obtained from one of: *Flammulina velutipes*, *Agrocybe aegerita*, or *Coprinus comatus*, or any combination thereof, wherein said enzyme is active at a pH of 1.9-6.3.

In another embodiment is provided a method for treating an oxalate-related medical condition in a subject. The method comprises administering a therapeutically effective amount of at least one oxalate degrading enzyme containing composition to a subject in need. The oxalate-related medical condition includes but is not limited to one of: primary hyperoxaluria, autism, secondary hyperoxaluria, Crohn's Disease, inflammatory bowel disease, colitis, cardiac conductance disorder, urolithiasis, vulvodynia, oxalosis associated with end-stage renal disease, bariatric surgery, and other enteric disease states. In a further embodiment, the at least one oxalate degrading enzyme comprises an enzyme that is active at a pH of 1.9-6.3. In an alternate embodiment the at least one oxalate degrading enzyme comprises an enzyme that is active at a pH of 5.5-8.0.

If the enzyme is active around neutral pH of 5.5-8.0, but is not stable at acid pH, the enzyme containing compositions or formulated enzyme can be incorporated into a capsule or tablet and the capsule or tablet can be further coated with acid protection film/membrane to aid the capsule or tablet to pass through the stomach. When the capsule or tablet reaches the small intestine or large intestine, where the pH is 6.5-7.5, much higher than the stomach, the coated film/membrane will dissolve/break to release the enzyme containing compositions or formulated enzyme. The enzyme will degrade oxalate in the small and/or large intestines. This technology is well known for those who are skilled in the art.

In another embodiment the at least one oxalate degrading enzyme comprises at least one of: oxalate-oxidase (OxOx), and/or oxalate decarboxylase (OxDC). In a further embodiment, the at least one oxalate degrading enzyme is obtained from one of: *Flammulina velutipes*, *Agrocybe aegerita*, or *Coprinus comatus*, or any combination thereof, wherein said enzyme is active at a pH of 1.9-6.3.

In another embodiment, the patient in need is determined by the conditions the patient exhibits. As aforementioned, the exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

In a more particular embodiment, the administration step is by oral administration. Compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

In another embodiment of the present invention, a method for treating an oxalate-related medical condition is provided. The method includes coadministering to a subject in need of such treatment a therapeutically effective amount of a first composition, wherein the first composition releases enzymes in the stomach of the subject, and a second composition, wherein the second composition releases enzymes in the intestinal tract of the subject. When the enzymes are released, the first composition degrades oxalate in the stomach, and the second composition degrades oxalate in the intestinal tract. The method is provided wherein the coadministration can be either sequential or simultaneous. The first and second compositions may be administered by the same or by different mode of delivery. The first and second compositions may include at least one of OxOx or and OxDC, respectively, or OxDC and OxOx, respectively.

There is provided in a further embodiment, an oxalate degrading composition derived from a fungal source. The composition includes at least a first powder and a second powder. The first powder includes at least one oxalate degrading enzyme, wherein the first powder releases the at least one oxalate degrading enzyme at a pH within a pH range of 1.9-5.5. The second powder comprising at least one oxalate degrading enzyme, wherein the second powder releases the at least one oxalate degrading enzyme at a pH within a pH range of 5.5-8.0. The oxalate degrading enzyme may be associated with a polymer, and may comprise OxOx and/or OxDC.

All patents, patent applications and references included herein are specifically incorporated by reference in their entireties. It should be understood, of course, that the foregoing relates only to exemplary embodiments of the present invention and that numerous modifications or alterations may be made therein without departing from the spirit and the scope of the invention as set forth in this disclosure. Although the exemplary embodiments of the present invention are provided herein, the present invention is not limited to these embodiments. There are numerous modifications or alterations that may suggest themselves to those skilled in the art.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Formulation:

Microencapsulation is widely applied for controlled release, or enteric coating for modification of food or drug flavor/taste, or protection of the drug component from acid or enzyme inactivation. There are many different physical and chemical approaches to prepare microencapsulation. Spray drying and lyophilization are two approaches that have a long existing industrial process with rich experience. The process is relatively simple for scaling up and relatively inexpensive.

There are many natural and synthetic polymers for microencapsulation selection development including chitosan, gelatin, alginate, pectin, and the Eudragit polymer series such as L-100 55. The keys for selecting polymers are their compatibility with the enzyme and the solubility in the GI tract. For example, the selected polymer should not reduce the stability of the enzymes. Since the formulated enzymes are expected to work throughout the entire GI tract, the microencapsulated enzyme particles should stay intact throughout the GI tract, but also should have hydrophilic pores for water and oxalate movement. To maintain particle formation, the selected polymer can either be insoluble at pH 2-8, but form small hydrophilic pores for oxalate and water movement, or the polymer can be soluble, but cross-linked by a chemical method or a physical method that make the water soluble polymer insoluble.

Chitosan has been successfully used to prepare microencapsulated particles by spray drying and it contains large numbers of free amino groups for chemical cross-linking by several cross-linkers including genipin. In our primary data, chitosan has been shown to extend the upper activity limit from pH 6.5 to pH 7.0 of the OxDC from *Coprinus* Cometus, which allows the enzyme to be active in most segments of the GI tract. By controlling manufacturing conditions and raw materials, chitosan can be produced in a broad range of molecular weights and various degrees of deacetylation to fit different application purposes. Molecular weight and degree of deacetylation significantly affect chitosan/water interactions. Chitosan usually dissolves in water at acidic pH (pH<4), but its solubility in water is affected by its molecular size and degree of deacetylation, where small molecular weight and high degree of deacetylation make the polymer more soluble in relatively high pH (for example, pH<5), but larger molecules of chitosan with relative low degree of deacetylation only dissolve at very acid pH (for example, pH<3). Molecular weight and degree of deacetylation of chitosan also significantly affect chitosan/enzyme interactions. Larger molecules of chitosan with relative low degree of deacetylation may microencapsulate enzymes more efficiently due to its hydrophobic interactions between enzyme and chitosan molecules. For example, two OxDC enzymes from *Boletus Flaviporus* and *Coprinus Cometus* are both stable at very acidic pH (pH 2-3), which makes it possible to use large chitosan molecules with relative low degrees of deacetylation. These chitosan molecules can slowly dissolve at a very low pH (for example, pH 2.2) during formulation, but may not dissolve even in the stomach once formulated as particles. Thus, cross-linking may not be required and a small ratio of chitosan:enzyme may be achievable, which may yield highly active products due to a low ratio of excipient:enzyme and no activity losses due to chemical cross-linking.

Gelatin or plant source proteins as representatives of protein polymers are also common formulation components. The solubility of protein microencapsulated particles in water can be reduced by a suitable chemical cross-linker such as genipin.

Alginate and pectin, similar to each other, are representatives of the polymers containing rich carboxyl groups, which can dissolve in water at neutral or alkaline pH. The formulated particles will dissolve in water as well, but the solubility of the formulated particles could be limited by cross-linking with $Ca^{2+}$ or genipin.

The polymers from the Eudragit polymer series, for enteric coating or sustained release formulations, are good candidates for protecting the enzymes from protease digestion and can be easily incorporated into the spray drying process. These polymers either are insoluble or soluble at high pH (5.5-7.0) and no cross-linking is required.

Spray drying conditions may change with polymer selection, compositions, and requirements of spray drying products. Therefore, spray drying under several different conditions to achieve microencapsulation will need to be evaluated.

The Eudragit polymer series for enteric coating or sustained release formulations are good candidates for protecting enzymes from protease digestion. Enzymes may be mixed with these polymers at a series of ratios, and certain excipients may be incorporated to protect the enzymes from the spray drying process, provide long term storage properties, and/or modify the properties of the final particles such as water and oxalate permeability.

Examples

Example 1: Assays

Activity Assay:

Liquid samples including supernatant, extraction and enzyme solutions were directly assayed for activity, whereas solid samples including pellet and dry powder were assayed after re-suspension with DI water. Fourty microliters of liquid sample or solid sample suspension was incubated with 360 μl of 2 mM oxalate in 50 mM citrate buffer, pH 3.5, at 37° C. for 10-60 min. The reaction was quenched by the addition of 100 μL 0.5 N NaOH. The reaction mixture was immediately centrifuged. The supernatant is diluted 10 times and then analyzed by an HPLC method to detect oxalate and formate. One unit of activity is defined as the amount of enzyme required to produce 1 μmole of formate from oxalate under the above conditions within one minute.

OxOx activity was also measured by monitoring hydrogen peroxide production through a horseradish peroxidase catalyzed color reaction: 10 μl of liquid sample or solid suspension was incubated with 9900 of 2 μmole of oxalate, 0.3 mg of 1, 4-amino antipyrine, 3.0 mg phenol and five units of peroxidase in 50 mM phosphate buffer, pH 7.0, at 37° C. for 5 min. After five minutes the absorbance at 510 nm was measured along with the control. One unit of activity is defined as the amount of enzyme required to produce 1.0 μmole of hydrogen peroxide under the above conditions.

Stability in Simulated Gastric Fluid (SGF):

SGF was prepared according to the USP (United States Pharmacopeia) method: 2 g of NaCl, 7 ml of concentrated HCl, and 3.2 g of pepsin, filled with water to 1 liter. Sample suspensions were treated with SGF: 0.4 mL of sample mixed with 0.6 mL of SGF at 37° C. and mixed for 10 mM, then neutralized with 0.1 mL of 500 mM NaOH. The suspension was centrifuged to remove supernatant and the pellet was immediately tested for activity as described previously. For solution samples treated with SGF: 0.4 mL of sample was mixed with 0.6 mL of SGF and incubated at 37° C. for 10 mM, then neutralized with 500 mM NaOH and immediately tested for activity as described previously.

Stability in Simulated Intestinal Fluid (SIF):

SIF was prepared according to USP (United States Pharmacopeia): 6.8 g of monobasic potassium phosphate in 250 mL of water, mix, and add 77 mL of 0.2 N sodium hydroxide and 500 mL of water. Add 10.0 g of pancreatin, mix, and adjust the resulting solution with either 0.2 N sodium hydroxide or 0.2 N hydrochloric acid to a pH of 6.8±0.1. Dilute with water to 1000 mL. Sample suspensions were treated with SIF: 0.4 ml of sample mixed with 0.6 ml of SIF at 37° C. and shaked for 10 min, then neutralized with 0.1 ml of 500 mM NaOH. The suspension was centrifuged to remove supernatant and the pellet was immediately tested for activity as described previously. For solution sample treated with SIF: 0.4 ml of sample was mixed with 0.6 ml of SIF and incubated at 37° C. for 10 mM, then neutralized with 500 mM NaOH and immediately tested for activity as described previously.

Thermal Stability:

To demonstrate thermal stability, suspended pellets or solution samples were incubated at 50-85° C. in 5° C. intervals for 10 mM, and then immediately cooled on ice. The treated samples were tested for activity as described previously.

Enzyme Functional pH Range:

Samples were assayed as described earlier except that a series of buffers within a pH range of 1.9-8.0 were used. These buffers were composed of 50 mM citrate buffer for pH 2.0-5.5, or 50 mM phosphate buffer for pH 6.0, 6.5, 7.0, 7.5 and 8.0.

Example 2:OxDC Activity in Mushrooms

Mushrooms collected from nature were identified and those purchased from supermarkets were translated to their Latin names. These mushrooms were cleaned and homogenized in the presence of deionized (DI) water. The homogenized samples were separated into supernatant and pellet fractions by centrifugation and both fractions were tested for oxalate-degrading activity. To determine specific activity/gram of dry weight, 10-15 grams of each pre-weighed strain of mushroom were dried at approximately 60° C. to a constant weight. The pellet fractions were further washed with water with a dilution factor of 1:50, then re-suspended in water for testing the pH activity profile, stability in SGF, and thermal stability.

Approximately 100 different species of mushrooms were tested under this invention as showed in Table 2, and 77 of them exhibited oxalate-degrading activity greater than 0.5 unit per gram of dried mushroom material. In most cases, the oxalate degrading activity was associated to OxDC activity, because an equal mole amount of formate was detected. Considering that the oxalate degrading activity from these mushrooms could be affected by the age of the mushroom, growth conditions, and handling process, the number of mushrooms that may produce oxalate-degrading enzyme during their life cycle, may be even more. However, majority of the mushrooms showed OxDC activity, indicating that this enzyme is a common enzyme amongst fungi.

TABLE 2

OxDC Activity from Select Fungi

| Names | Activity (u/g dry material) |
|---|---|
| Dentinum repandum | 4 |
| Amanita solitarii-formis | 0 |
| Suillur birfellur | 0 |
| Russula virescens | 2 |
| Amanita praelongispora | 0 |
| Armillaria tabescens | 3.6 |
| Cantharellur cinnabarinur | 0.4 |
| Boletur rubellus var fraternus | 1.5 |
| Collybia acervata | 0.3 |
| Crepidotus mollis | 3.5 |
| Boletur subglabripes | 0.2 |
| Boletus ornatipes | 2.3 |
| Lepiota rachodes | 0 |
| Polyporus elegans | 3.1 |
| Agricus bisporus | 0 |
| Pluteus cervinus | 3.8 |
| Agricus bisporus | 0 |
| Scleroderma citrinum | 3.8 |
| Pleurotus ostreatus | 0.6 |
| Xerula radicata | 5 |
| Thelephora vlalis | 3.3 |
| Clitocybe | 0.4 |
| Cortinarius cedretorun | 1.8 |
| Russula amoenolens | 0 |
| Lactarius indigo | 3.9 |
| Hygrophorus chrysodon | 0 |
| Russula ematica ined | 0 |
| Cantharellus cibarius | 0 |
| Lactarius tomentosu | 0 |
| Pleorotus | 0 |
| Russula densifolia | 2.6 |
| Amanita rhopalopus | 3 |
| Gymnopilus | 0 |
| Clitocybe hydrograma | 1 |
| Hypholoma | 0 |
| Lactarius luteolus | 0 |
| Marasmius rotula | 0 |
| Amanita vaginata | 0 |
| Amanita gemmata | 3.3 |
| Amanita pachycolia | 0 |
| Cortinarius lewisii | 2.7 |
| Cortinarius delibutus | 0 |
| Pleurotus eryngii | 4.3 |
| Inocybe rimosa | 5.5 |
| Lactarius atrorividus | 3.6 |

TABLE 2-continued

OxDC Activity from Select Fungi

| Names | Activity (u/g dry material) |
|---|---|
| Lepiota cristata | 0 |
| Nolanea verna | 0 |
| Plutus australis | 0 |
| Russula cyanoxhanth | 0.9 |
| Scleroderma polyrhizum | 3.6 |
| Lentinula edodes | 1 |
| Lentinula edodes | 1.5 |
| Hypsizygus tessellatus | 3.4 |
| Flammulina velutipes | 4.4 |
| Morchella esculenta | 0 |
| Leucangia carthusiana | 20 |
| Tuber oregonense | 12 |
| Grifola frondosa | 0.7 |
| Tremellodendropsis semivestitum | 0 |
| Strobilomyces confusus | 0 |
| Mutinus Caninus | 0 |
| Austroboletus subflavidus | 0 |
| Austroboletus gracilis | 0 |
| Boletus rubricitrinus | 2.1 |
| Boletus pallidus | 0 |
| Boletus subglabripes | 0 |
| Tylopilus conicus | 0 |
| Boletus fairchildianus | 0 |
| Boletus fraternus | 1.1 |
| Gyroporus subalbellus | 0.6 |
| Leucoagaricus americanus | 1.2 |
| Omphalotus olearius | 3.9 |
| Coprinus disseminatus | 0.6 |
| Suillus cothurnata | 0 |
| Xeromphalina campanella | 0 |
| Amanita brunnescens | 1 |
| Russula helerophylla | 0.2 |
| Mycorrhaphium adustum | 2.4 |
| Armillaria tabescense | 2.9 |
| Amanita aspera | 0 |
| Pleurotus ostreatus | 0 |
| Russula mariae | 0 |
| Pleurotus ostreatus 2nd | 0 |
| Agaricus blazei | 0 |
| Boletus flaviporus | 0.9 |
| Russula pectintoides | 0.6 |
| Lentinula boryana | 0.3 |
| Amanita mutabilis | 1.6 |
| Gyroporus subalbellus 2nd | 2.5 |
| Collybia peronata | 2.9 |
| Lactarius corrugis | 1.2 |
| Rhodocybe | 1.3 |
| Macrocybe titaus | 1.2 |
| Hydnum repandum | 0 |
| Collybia | 0.9 |
| Pluteus | 0.3 |
| Lactarius yazooensis | 1.3 |
| Leccinum insigne | 0.4 |
| Psathyrella candolleana | 0 |
| Coprinus comatus | 1 |
| Polyporus tuberaster | 2.3 |
| Agrocybe aegerita | 3.5 |
| Trametes versicolor | 2.7 |
| Ganoderma lucidum | 2 |
| Hypsizygus ulmarius | 4 |
| Lentinula edodes (warm) | 1.2 |
| Lentinula edodes (cold) | 1.7 |
| Lentinula edodes (wide range) | 2 |
| Stropharia rugoso-annulatat | n/a = 0 |
| Hericuium erinaceus | 0 |
| Laetiporus conifericola | 0 |
| Pholiota nameko | 0 |

Example 3: OxOx Activity in Mushrooms

Samples tested in Example 2 which showed little to no formate production as compared to oxalate degraded were further tested for production of hydrogen peroxide to determine the presence of OxOx activity. OxOx activity was detected from 3 mushrooms: *Russula amoenolens*, *Lactarius tomentosu* and *Agaricus blazei* in the contents with 1.2, 4.7 and 2.1 units per gram of dried mushrooms, respectively.

Example 4: Production of OxDC by Fermentation

Mushroom fungi cultured by fermentation are listed in Table 3. Cultures were grown on malt agar plates containing (w/v): 3% malt extract, 0.5% soy peptone, and 1.5% agar, and maintained at 4° C. All fungi were cultivated in malt extract liquid culture medium (pH 6.0) containing (w/v): 2.0% glucose, 0.2% (w/v) yeast extract, 2% malt extract, 0.1% $KH_2PO_4$, 0.03% $Na_2HPO_4.2H_2O$, and 0.05% $MgSO_4.7H_2O$. The medium was autoclaved at 121° C. for 20 min. Cultivation and production of OxDC was performed in 1.0 L flasks containing 250 mL of liquid medium and cultured at 25° C. for 10-20 days to reach

TABLE 3

Production of OxDC from Select Fungi by Fermentation

| Names | Activity (U/g) | Induction pH |
|---|---|---|
| Grifola frondosa | 0.7 | 3 |
| Coprinus comatus | 18 | 3.2 |
| Polyporus tuberaster | 8.2 | 3 |
| Agrocybe aegerita | 20 | 3 |
| Trametes versicolor | 7.1 | 2.5 |
| Ganoderma lucidum | 5.6 | 2.5 |
| Hypsizygus ulmarius | 14 | 3.2 |
| Lentinula edodes (warm) | 4.5 | 2.8 |
| Lentinula edodes (cold) | 6.7 | 2.8 |
| Lentinula edodes (wide range) | 5.2 | 2.8 |
| Flammulina velutipes | 15 | 3 |
| Stropharia rugoso-annulata | n/a = 0 | 0 |
| Hericium erinaceus | 0 | 0 |
| Laetiporus conifericola | 0 | 0 |
| Pholiota nameko | 0 | 0 |

10-30 g of wet mycelia per liter of culture. Then 1.0 M sulfuric acid, or 1.3 M phosphoric acid was added to adjust the pH to 2.0-3.5, and induce OxDC production. The pH was maintained by checking every 2 hours and adjusted by adding any of the above acid solutions. The actual induction pHs for these fungi are listed in Table 3. After 3 days of induction, mycelia were harvested by centrifugation and re-suspended in water. The mycelia suspension was homogenized and centrifuged. The supernatant and pellet both were collected. The supernatant was directly tested for OxDC activity. The supernatants usually contained 5-15% of the total OxDC activity and were not used for further testing. The pellet was washed with water in a 1:50 dilution factor and then re-suspended for testing OxDC activity. OxDC activity from these pellet suspensions are given in Table 3.

Example 5: Production of OxOx by Plants

Barley or wheat seeds supported by stainless steel mesh were half emerged in water for germination and growth at room temperature. After 10-12 days, the young plants were harvested and cut into small pieces for homogenization. The homogenized sample was centrifuged. The supernatant and pellet both were collected and tested for OxOx activity.

100 grams of fresh leafs from *Bougainvillea buganvilla* and 50 grams of ten day old *Sorghum vulgaris* plants were homogenized separately in cold deionized (DI) water. The homogenized samples were passed over a 200-micron sieve and then separated into supernatant and pellet fractions by centrifugation at 3500 g for 10 minutes. The pellet was re-suspended in water and both fractions were tested for oxalate-degrading activity. To determine specific activity/gram of dry pellet weight, pellet from 10 mL of suspension was collected by centrifugation at 3500 g for 30 minutes and then dried at approximately 60° C. to a constant weight.

OxOx from both Barley and wheat is stable and active in acid pH within a range of 2.0-5.5, but OxOx from *Bougainvillea buganvilla* leaves is stable and active around neutral pH with a range of 5.5-8.0.

Example 6: Demonstration of Enzyme Stability in Simulated Gastric Fluid

OxDC from mushrooms or fermented mycelia and OxOx from mushrooms were treated with SGF to simulate the harshest condition in the human stomach as described in Example 1. The mushrooms or mycelia that retained OxDC or OxOx activity after SGF treatment are given in Table 4.

TABLE 4

OxDC and OxOx Remaining Activity from Select Fungi after SGF treatment

| Names | Remaining Activity (%) |
|---|---|
| Dentinum repandum | 101 |
| Russula virescens | 109 |
| Boletur rubellus var fraternus | 87 |
| Crepidotus mollis | 64 |
| Polyporus elegans | 89 |
| Scleroderma citrinum | 108 |
| Xerula radicata | 97 |
| Thelephora vlalis | 105 |
| Lactarius indigo | 102 |
| Russula densifolia | 113 |
| Inocybe rimosa | 94 |
| Lactarius atrorividus | 93 |
| Scleroderma polyrhizum | 111 |
| Lentinula edodes | 92 |
| Lentinula edodes | 93 |
| Flammulina velutipes | 92 |
| Omphalotus olearius | 96 |
| Mycorrhaphium adustum | 89 |
| Armillaria tabescense | 47 |
| Russula pectintoides | 68 |
| Lactarius yazooensis | 88 |
| Leccinum insigne | 65 |
| Polyporus tuberaster | 67 |
| Agrocybe aegerita | 96 |
| Trametes versicolor | 99 |
| Ganoderma lucidum | 103 |
| Lentinula edodes (warm) | 93 |
| Lentinula edodes (cold) | 90 |
| Lentinula edodes (wide range) | 91 |
| Agaricus blazei (OxOx) | 91 |
| Lactarius tomentosu (OxOx) | 91 |

Example 7: Enzymes that are Active in the Entire pH Range the Human Stomach can Experience OxDC from mushrooms or fermented mycelia and OxOx from mushrooms and plants were tested for oxalate degrading activity from pH 1.9-5.5. Several of these enzyme preparations were even tested for activity up to pH 7.5, as described in Example 1. The results are given in Table 5. The optimum pH range is defined by an enzyme with at least 40% of its highest activity at any pH within the range and the active pH range is defined as showing at least 5% of its highest activity at any pH within the range. Many of these enzymes are active from pH 1.9-5.3 or even broader pH 1.9-6.3, thus covering the entire pH range that the human stomach can experience. It should be noted that enzyme activity at pH lower than 1.9 was not examined, but it is reasonable to assume that some of these enzymes should be active at pH lower than 1.9, which show an optimum activity at pH 1.9.

TABLE 5

Optimum and Active pH Ranges of OxDC or OxOx from Select Fungi

| Names | Optimum pH range | Active pH range |
|---|---|---|
| Dentinum repandum | 1.9-3.2 | 1.9-4.3 |
| Russula virescens | 1.9-2.7 | 1.9-4.3 |
| Boletur rubellus var fraternus | 1.9-3.2 | 1.9-4.3 |
| Crepidotus mollis | 3.2-4.3 | 1.9-5.3 |
| Polyporus elegans | 1.9-2.7 | 1.9-3.2 |
| Scleroderma citrinum | 1.9-3.2 | 1.9-5.3 |
| Xerula radicata | 2.7-3.2 | 1.9-5.3 |
| Thelephora vlalis | 1.9-2.7 | 1.9-4.8 |
| Lactarius indigo | 1.9-3.2 | 1.9-4.3 |
| Russula densifolia | 1.9-3.2 | 1.9-4.3 |
| Pleurotus eryngii | 3.5-4.5 | 3.2-5.3 |
| Inocybe rimosa | 2.7-3.2 | 1.9-4.8 |
| Lactarius atrorividus | 1.9-3.2 | 1.9-4.3 |
| Sderoderma polyrhizum | 1.9-3.2 | 1.9-4.3 |
| Lentinula edodes | 2.5-3.0 | 1.9-5.5 |
| Hypsizygus tessellatus | 3.5-4.0 | 2.5-5.5 |
| Flammulina velutipes | 2.7-4.0 | 1.9-5.5 |
| Leucangia carthusiana | 2.7-4.0 | 1.9-5.5 |
| Tuber oregonense | 2.7-4.0 | 1.9-5.5 |
| Grifola frondosa | 2.7-3.2 | 1.9-3.2 |
| Boletus rubricitrinus | 1.9-2.7 | 1.9-3.2 |
| Boletus fraternus | 1.9-3.2 | 1.9-5.3 |
| Gyroporus subalbellus | 1.9-3.2 | 1.9-5.3 |
| Leucoagaricus americanus | 1.9-3.2 | 1.9-4.3 |
| Omphalotus olearius | 1.9-4.3 | 1.9-5.3 |
| Coprinus disseminates | 2.7-3.2 | 1.9-4.3 |
| Amanita brunnescens | 2.7-3.2 | 1.9-4.3 |
| Mycorrhaphium adustum | 1.9-2.7 | 1.9-4.3 |
| Armillaria tabescense | 2.7-3.2 | 1.9-4.3 |
| Boletus flaviporus | 2.7-5.3 | 1.9-6.3 |
| Russula pectintoides | 1.9-4.3 | 1.9-5.3 |
| Amanita mutabilis | 2.7-3.2 | 1.9-5.3 |
| Gyroporus subalbellus $2^{nd}$ | 1.9-3.2 | 1.9-5.3 |
| Collybia peronata | 1.9-3.2 | 1.9-4.3 |
| Rhodocybe | 1.9-3.2 | 1.9-4.3 |
| Macrocybe titaus | 2.7-3.2 | 1.9-4.3 |
| Lactarius yazooensis | 2.7-4.3 | 1.9-5.3 |
| Leccinum insigne | 2.7-3.2 | 1.9-4.8 |
| Coprinus comatus | 3.2-6.0 | 1.9-6.3 |
| Polyporus tuberaster | 1.9-3.2 | 1.9-4.8 |
| Agrocybe aegerita | 2.7-3.7 | 1.9-6.3 |
| Trametes versicolor | 1.9-2.3 | 1.9-4.3 |
| Ganoderma lucidum | 1.9-2.7 | 1.9-4.5 |
| Hynsizygus ulmarius | 3.0-4.0 | 1.9-6.3 |
| Lentinula edodes (warm) | 2.5-3.0 | 1.9-5.5 |
| Lentinula edodes (cold) | 2.5-3.0 | 1.9-5.5 |
| Lentinula edodes (wide range) | 2.5-3.0 | 1.9-5.5 |
| Agaricus blazei (OxOx) | 2.5-3.0 | 1.9-4.8 |
| Lactarius tomentosu (OxOx) | 2.5-3.0 | 1.9-4.3 |

Figure 1:
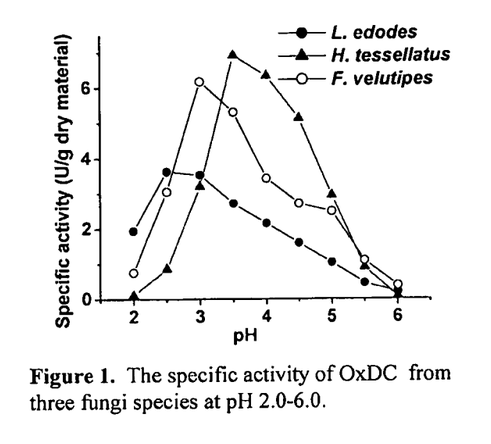
FIG. 1 shows a graph illustrating the pH activity profile of OxDC from three fungi species at pH 1.9-6.3.

As shown in FIG. 1, OxDC from three selected mushrooms show significantly different pH activity profiles. OxDC from *L. edodes* shows activity at pH 2.0-5.0 with optimum activity at pH 2.5-3.0, while OxDC from *F. velutipes* shows activity at pH 2.5-5.0 with optimum activity at pH 3.0-3.5. Furthermore, OxDC from *H. tessellatus* reveals activity at pH 3.0-5.0 with optimum activity at pH 3.5-4.0.

Example 8: Thermal Stability

OxDC from mushrooms or fermented mycelia and OxOx from mushrooms were heat treated from 50 to 80° C. as described in Example 1. The temperatures that retained more than 70% of the original OxDC or OxOx activity are given in Table 6.

TABLE 6

Thermal stability of OxDC and OxOx from Select Fungi

| Names | Temperature (° C.) |
|---|---|
| *Scleroderma citrinum* | >80 |
| *Flammulina velutipes* | 75 |
| *Omphalotus olearius* | 75 |
| *Boletus flaviporus* | 65 |
| *Russula pectintoides* | 75 |
| *Lactarius yazooensis* | 70 |
| *Coprinus comatus* | 75 |
| *Agrocybe aegerita* | 75 |
| *Agaricus blazei* (OxOx) | 70 |

Figure 2:
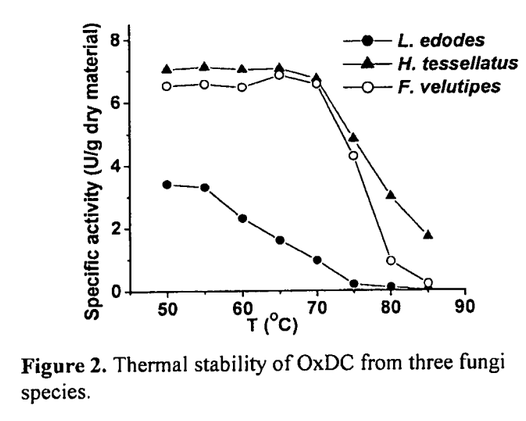
FIG. 2 shows thermal stability of OxDc from three fungi species
Figure 3:
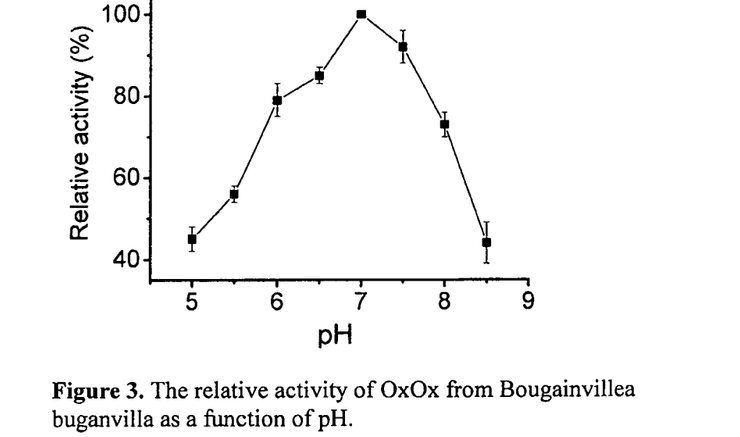
FIG. 3 shows a graph illustrating the pH activity profile of OxOx from *Bougainvillea buganvilla* at pH 5.0-8.5

As shown in FIG. 2, OxDC from *L. edodes* was determined to be thermally stable at 55° C., lower than OxDC from *H. tessellates* and *F. velutipes*, which both were stable up to 70° C., respectively.

Example 9: Degradation of Food Oxalate in Simulated Gastric Conditions

Food mixtures were produced by mixing and homogenizing (w/w): 5% spinach, 15% cooked chicken, 40% cooked rice and 40% water. The total oxalate content was 90 mg per 100 g of this food mixture. The average daily oxalate intake from Western diets is 50-250 mg. Three conditions were evaluated to simulate snacks and full meals. The testing experiments were scaled down five times from the actual average amount of stomach juice (150 mL).

The food mixture was mixed with simulated gastric fluid: 10, 40 and 200 g of food mixture was mixed with 30 ml of simulated gastric fluid (84 mM HCl with 3.2 mg/ml pepsin) and then filled with water to 40, 160 and 800 g, respectively. A homogenized mycelia suspension, which was made from fermentation of *Agrocybe aegerita* and contained approximately 15 units of oxalate decarboxylase per gram of suspension or 150 units per gram of dried mycelia powder, was used to degrade oxalate from these food mixtures. 5, 20 and 100 g of the homogenized mycelia suspensions were added to these food mixtures, respectively. The final pH of the three reaction mixtures was 2.3, 3.4 and 5.2. The mixtures were mixed slowly and maintained at 37° C. Samples were taken at 0, 5, 10, 20, 30, and 40 minutes for soluble oxalate determination. Soluble oxalate was measured by an HPLC method as described in Example 1 for the oxalate decarboxylase activity assay. The soluble oxalate concentrations dropped from 0.82, 0.66 and 0.43 mM for the three cases from small size to large size food mixtures, respectively, to less than 0.1 mM in 10 minutes and further dropped to less than 0.03 mM for all three cases after 40 minutes.

Example 10

Figure 4:
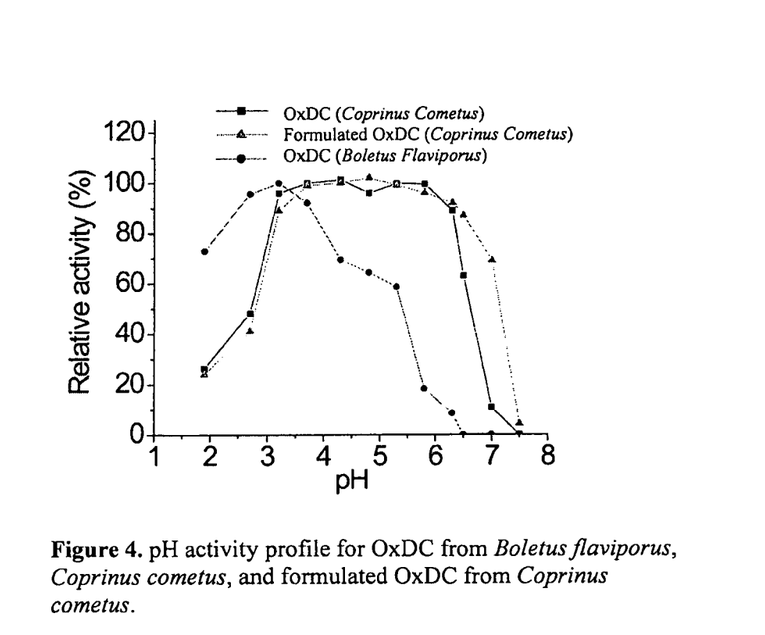
FIG. 4 pH activity profile for OxDC from *Boletus flaviporus, Coprinus cometus*, and formulated OxDC from *Coprinus cometus*
Figure 5:
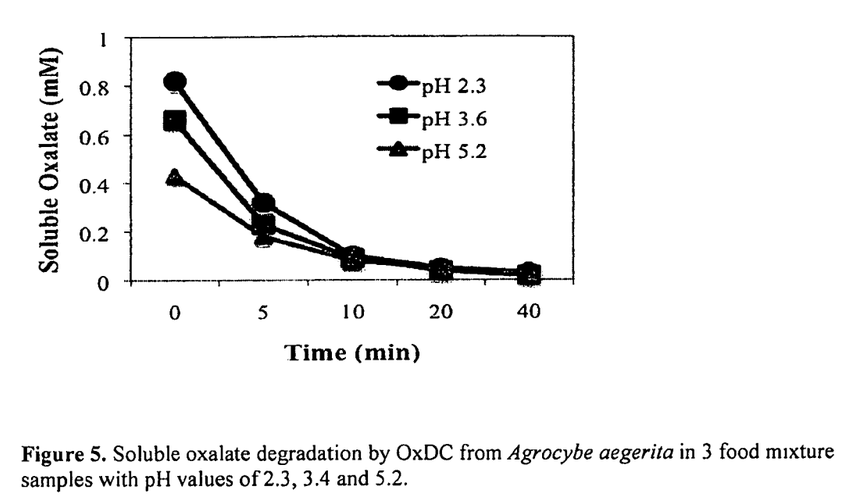
FIG. 5 Soluble oxalate degradation with OxDC from *Agrocybe aegerita* in 3 food mixture samples with pH values of 2.3, 3.4 and 5.2.

Functional pH shift from pH 6.5 to 7.0 by immobilization 20 mg of crude enzyme was obtained from the cultured fungi homogenized supernatant, which contained 10 Units/mg of protein. The crude enzyme was mixed with 1% of chitosan solution (>92% deacetylation) at pH 4.0, then 0.3% tripolyphosphate (TPP) solution was added until most of the chitosan formed particles. The particles were collected by centrifugation at 2000 g for 10 minutes and re-suspended in water. Glutaraldehyde was added to a final concentration of 1% with pH adjusted to pH 8.0 with 1 N NaOH. The cross-linking reaction was for 10 minutes at 25° C. and was then diluted 10 times with water. The cross-linked particles were immediately washed with water at a dilution rate of 1000 to remove most free glutaraldehyde and the washed particles were used for the functional pH assay and the activity results shown in FIG. 4.

Identification of the fungal species found in the culture collections can be obtained from Table 7 by the accession numbers provided.

TABLE 7

Fungal Species Found in Culture Collections

| Names | Accession Numbers |
|---|---|
| *Dentinum repandum* | PSU 558 |
| *Amanita solitarii-formis* | ATCC 26842 |
| *Suillus birfellur* | |
| *Russula virescens* | FMRC SO16 |
| *Amanita praelongispora* | BPI 750680 |
| *Armillaria tabescens* | ATCC 62415 |
| *Cantharellus cinnabarinus* | FMRC SO2021 |
| *Boletus rubellus* var *fraternus* | BPI 781712 |
| *Collybia acervata* | BPI 1102144 |
| *Crepidotus mollis* | ATCC 96569 |
| *Boletus subglabripes* | BPI 781892 |
| *Boletus ornatipes* | BPI 781195 |
| *Lepiota rhacodes* | NCIM 1155 |
| *Polyporus elegans* | BPI 1113147 |
| *Agaricus bisporus* | FGSC 10389 |
| *Pluteus cervinus* | PSU 571 |
| *Agaricus bisporus* | FGSC 10389 |
| *Scleroderma citrinum* | UU F-149335 |
| *Pleurotus ostreatus* | PSU 610 |
| *Xerula radicata* | BPI 769566 |
| *Thelephora vialis* | CGMCC 550* |
| *Clitocybe aurantiaca* | PSU 3 |
| *Cortinarius cedretorum* | BPI 774972 |
| *Russula amoenolens* | CBS 133* |
| *Lactarius indigo* | BPI 759669 |
| *Hygrophorus chrysodon* | BPI 1104446 |
| *Russula ematica ined* | FMRC SO15 |
| *Cantharellus cibarius* | PSU 560 |
| *Lactarius torminosus* | BPI 763347 |
| *Pleorotus herbrodensis* | PSU 850 |
| *Russula densifolia* | CBS 133* |
| *Amanita rhopalopus* | LSID 308584 |
| *Gymnopilus spectabilis* | FMRC SO48 |
| *Clitocybe hydrogramma* | BCRC 59* |
| *Hypholoma dispersum* | PSU 69 |
| *Lactarius luteolus* | PSU W59 |
| *Marasmius rotula* | ATCC 62251 |
| *Amanita vaginata* | FMRC SO04 |
| *Amanita gemmata* | FMRC SO0121 |
| *Amanita pachycolea* | LSID 109592 |
| *Cortinarius lewisii* | LSID 360163 |
| *Cortinarius delibutus* | CCBAS 558* |
| *Pleurotus eryngii* | ATCC 36047 |
| *Inocybe rimosa* | CBS 210.55 |
| *Lactarius atroviridis* | LSID 226377 |
| *Lepiota cristatiformis* | BPI 751892 |
| *Nolanea verna* | LSID 283581 |
| *Pluteus australis* | LSID 441053 |
| *Russula cyanoxhanth* | CBS 133* |
| *Scleroderma polyrhizum* | BPI 711197 |
| *Lentinula edodes* | ATCC 28759 |
| *Lentinula edodes* | ATCC 38222 |
| *Hypsizygus tessellatus* | FMRC SO13122 |
| *Flammulina velutipes* | FP LCTTFV |
| *Morchella esculenta* | PSU 744 |
| *Leucangium carthusianum* | LSID 169340 |
| *Tuber oregonense* | LSID 515123 |
| *Grifola frondosa* | ATCC 11936 |
| *Tremellodendropsis semivestita* | LSID 169340 |

TABLE 7-continued

Fungal Species Found in Culture Collections

| Names | Accession Numbers |
| --- | --- |
| Strobilomyces confusus | LSID 515123 |
| Mutinus Caninus | PSU 182 |
| Austroboletus subflavidus | LSID 118437 |
| Austroboletus gracilis | LSID 118431 |
| Boletus rubricitrinus | BPI 781645 |
| Boletus pallidus | BPI 781208 |
| Boletus subglabripes | BPI 781892 |
| Tylopilus conicus | BPI 782426 |
| Boletus fairchildianus | LSID 309677 |
| Boletus fraternus | BPI 780755 |
| Gyroporus subalbellus | BPI 782362 |
| Leucoagaricus americanus | LSID 466261 |
| Omphalotus olearius | PSU W35 |
| Coprinus disseminatus | ATCC 46973 |
| Suillus cothurnatus | CBS 213.76 |
| Xeromphalina campanella | CBS 507.48 |
| Amanita brunnescens | BPI 750090 |
| Russula heterophylla | BPI 764312 |
| Mycorrhaphium adustum | BPI 348302 |
| Armillaria tabescense | BPI 747151 |
| Amanita aspera | BPI 750101 |
| Pleurotus ostreatus | PSU 628 |
| Russula mariae | BPI 764415 |
| Pleurotus ostreatus 2nd | PSU 598 |
| Agaricus blazei | ATCC 76739 |
| Boletus flaviporus | BPI 780557 |
| Russula pectinatoides | BPI 764603 |
| Lentinula boryana | PSU 787 |
| Amanita mutabilis | ATCC 26846 |
| Gyroporus subalbellus 2nd | BPI 782362 |
| Collybia peronata | ATCC 62243 |
| Lactarius corrugis | PSU W58 |
| Rhodocybe roseoavellanea | BPI 771252 |
| Macrocybe titans | LSID 443595 |
| Hydnum repandum | BPI 1102039 |
| Collybia dryophila | ATCC 62269 |
| Pluteus cervinus | PSU 571 |
| Lactarius yazooensis | LSID 116133 |
| Leccinum insigne | LSID 333018 |
| Psathyrella candolleana | PSU 32 |
| Coprinus comatus | ATCC 12640 |
| Polyporus tuberaster | CBS 786.84 |
| Agrocybe aegerita | ATCC 3645 |
| Trametes versicolor | ATCC 11235 |
| Ganoderma lucidum | ATCC 32471 |
| Hypsizygus ulmarius | PSU 412 |
| Lentinula edodes (warm) | PSU 376 |
| Lentinula edodes (cold) | PSU 375 |
| Lentinula edodes (wide range) | PSU 878 |
| Stropharia rugoso-annulatat | PSU 406 |
| Hericuium erinaceus | PSU 27 |
| Laetiporus conifericola | LSID 372852 |
| Pholiota nameko | ATCC 42261 |

BPI = USDA Agriculture Research Service Fungal Database
ATCC = American Tissue Culture Collection
PSU = Penn State University Mushroom Collection Center
FMRC = Florida Mycology Research Center
FGSC = Fungal Genetic Stock Center
FP = FungiPerfecti
UU = Uppsala University Botany Section
UA = University of Alberta Microfungus Collection
CGMCC = China General Microbiological Culture Collection Center
CCBAS = Culture Collection of Basidiomycetes
CBS = Centraalburea voor Schimmelcultures, Fungal and Yeast Collection
LSID = Index Fungorum
NCIM = National Collection of Industrial Microogranisms
BCRC = Bioresource Collection and Research Center
*These fungal species are found within these databases; however, no accession numbers are assigned.

What is claimed is:

1. An oxalate degrading composition, said composition comprising:
at least one first oxalate degrading enzyme obtained from a fungal source, formulated with a stabilizing polymer, wherein the at least one first oxalate degrading enzyme comprises an oxalate decarboxylase enzyme having at least 5% of its maximum activity to degrade oxalate at a pH of 1.9 and at least 5% of its maximum activity to degrade oxalate at a pH of 6.3; the polymer is one or more polymers selected from the group consisting of aminoalkyl methacrylate copolymer, methacrylic acid copolymer, methacrylic ester copolymer and ammonioalkyl methacrylate copolymer; and wherein said fungal source is selected from the group consisting of *Agrocybe aegerita*, *Boletus Flaviporus*, *Hypsizygus ulmarius* and *Coprinus comatus*.

2. The composition of claim 1, wherein said composition further comprises a second enzyme comprising an oxalate oxidase that is active at a pH of 5.0-8.0.

3. A method for reducing the amount of oxalate in a subject, comprising:
orally administering a therapeutically effective amount of the composition of claim 1, wherein said enzyme composition degrades soluble oxalate in the digestive tract of said subject, thereby reducing the amount of oxalate in the subject.

4. The method of claim 3, wherein said composition further comprises an oxalate oxidase enzyme isolated from a fungal or a plant source that is active at a pH of 5.0-8.0.

5. The method of claim 3, wherein said oxalate decarboxylase enzyme is isolated from said fungal source grown under fermentation conditions.

6. A method for treating an oxalate-related medical condition in a subject wherein said method comprises orally administering a therapeutically effective amount of the composition of claim 1 to the subject in need, wherein said oxalate-related medical condition is selected from the group consisting of primary hyperoxaluria, autism, secondary hyperoxaluria, Crohn's Disease, inflammatory bowel disease, colitis, cardiac conductance disorder, urolithiasis, vulvodynia, bariatric surgery and oxalosis associated with end-stage renal disease and related enteric disease states.

7. The method of claim 6, wherein said composition further comprises an oxalate oxidase enzyme that is active at a pH of 5.5-8.0.

8. The method of any one of claims 3 or 6, wherein said oxalate decarboxylase enzyme degrades soluble oxalate in the stomach of said subject.

* * * * *